United States Patent [19]

Chang

[11] Patent Number: 5,424,272

[45] Date of Patent: Jun. 13, 1995

[54] FATTY ALCOHOL COMPOSITION AND METHOD FOR CONTROLLING AXILLARY AND TERMINAL BUDS OF AGRONOMIC, HORTICULTURAL AND FORESTRY CROPS

[76] Inventor: In-Kook Chang, 9541 Remington Dr., Mentor, Ohio 44060

[21] Appl. No.: 108,149

[22] Filed: Aug. 13, 1993

Related U.S. Application Data

[63] Continuation of Ser. No. 772,058, Oct. 7, 1991, abandoned.

[51] Int. Cl.$^6$ ............................................. A01N 31/02
[52] U.S. Cl. ...................................... 504/184; 504/185
[58] Field of Search .................................. 504/184, 185

[56] References Cited

U.S. PATENT DOCUMENTS

| | | | |
|---|---|---|---|
| 3,253,904 | 5/1966 | Harrison | 71/2.6 |
| 3,326,664 | 6/1967 | Tso | 71/2.6 |
| 3,438,765 | 4/1969 | Tso et al. | 71/78 |
| 3,824,094 | 7/1974 | Tso | 71/78 |
| 3,852,057 | 12/1974 | Findley et al. | 71/78 |
| 4,627,869 | 12/1986 | Chang | 71/78 |

OTHER PUBLICATIONS

Steffens, G. L. et al. "Fatty Alcohol Inhibition of Tabacco Axillary and Terminal Bud Growth", *J. Agr. Food Chem.* 15:972–975 1967.

Nickell, L. G. *Plant Growth Regulators.* NY: Springer-Verlag. pp. 45–48. 1982.

North Carolina Cooperative Extension Sevice. "Flue-Cured Tobacco" 1992, pp. 65–67, 79.

Hawks et al. "Principles of Flue-Cured Tobacco Production". 1983. p. 252.

*Primary Examiner*—S. Mark Clardy
*Attorney, Agent, or Firm*—Renner, Kenner, Greive, Bobak, Taylor & Weber

[57] ABSTRACT

A composition mixture for controlling axillary and terminal buds of agronomic, horticultural and forestry crops including from about 5 to about 95 percent by weight of at least one first fatty alcohol having up to about 10 carbon atoms and from about 95 to about 5 percent by weight of at least one second fatty alcohol having at least 11 carbon atoms. A method according to the present invention includes contacting the crop buds with such a composition.

12 Claims, No Drawings

FATTY ALCOHOL COMPOSITION AND METHOD FOR CONTROLLING AXILLARY AND TERMINAL BUDS OF AGRONOMIC, HORTICULTURAL AND FORESTRY CROPS

This application is a continuation of Ser. No. 07/722,058, now abandoned, filed Oct. 7, 1991.

TECHNICAL FIELD

This invention relates to the control of axillary and terminal buds of agronomic, horticultural and forestry crops. More particularly, the present invention relates to controlling such buds while imparting low necrosis and phytotoxicity levels to the crops. Specifically, the invention relates to a composition and method for controlling such buds, which include a mixture of at least one fatty alcohol having up to about ten carbon atoms, and at least one fatty alcohol having at least eleven carbon atoms.

BACKGROUND OF THE INVENTION

It is known in the agronomic, horticultural and forestry crop raising industries, such as in tobacco farming, that the overall crop yield can be increased by removing axillary and terminal buds that would otherwise take away nutrients that can be directed toward another section of the plant. In tobacco farming, the leaves of the plant will grow larger more quickly if the axillary and terminal buds are removed.

One easy and yet time consuming and expensive method of removing axillary and terminal buds is to have a worker pinch, cut or otherwise remove the buds by hand. Because of the time and costs involved, chemical debudding agents have been developed.

As will be appreciated by one skilled in the art, it is necessary for a debudding agent to be active enough to sufficiently destroy or inhibit the growth of the buds, and yet it must not kill the plant itself, known as "necrosis", or impart hazardous phytotoxicity levels to the plant to make it unfit for human or animal use.

Fatty alcohols have been used as debudding agents. It is commercially known that 1-decanol is useful as a debudding agent because of its high activity in debudding and inhibiting bud growth and because it imparts low phytotoxicity to the plants themselves. One known preparation contains 1-decanol mixed with 1-octanol.

Fatty alcohols having higher than 10 carbon atoms have not been employed as debudding agents, because they are known to cause high necrosis and phytotoxicity in plants such as tobacco leaves. Those known compositions that do contain a fatty alcohol with more than 10 carbon atoms, have included these alcohols only as an unintentioned impurity imparted to the composition during manufacturing processes. These impurities are generally of about 3 percent by weight or less.

Even though the fatty alcohols having fewer than 10 carbon atoms showed the desired activity levels and the desired low levels of necrosis and phytotoxicity, these compounds are more toxic to humans and animals than the fatty alcohols having a larger number of carbon atoms.

For example, it is known that 2600 to 3100 milligrams per kilogram of 1-hexanol is considered lethal to fifty percent of a rabbit population (LD50), while the number is greater than 10,000 milligrams per kilogram for 1-dodecanol.

Furthermore, flammability hazards are greater with fatty alcohols having 10 or fewer carbon atoms than for those with a greater number of carbon atoms.

Therefore, debudding agents that have heretofore been commercially employed in the agronomic, horticultural and forestry industries have been those with fewer than 10 carbon atoms, because these alcohols cause less damage to the plants themselves. However, these alcohols with lower numbers of carbon atoms also present the most hazards because of their greater toxicity to humans and animals and the greater flammability hazards when compared to those fatty alcohols having greater than 10 carbon atoms.

Therefore, a need exists for a chemical debudding agent which has the high activity and low necrosis and phytotoxicity inducing levels of fatty alcohols having less than 10 carbon atoms, and the high stability and low human toxicity levels of the fatty alcohols having greater than 10 carbon atoms. No single alcohol or mixture of alcohols heretofore known, has possessed or been expected to possess these characteristics.

SUMMARY OF INVENTION

It is therefore, an object of the present invention to provide a composition for controlling axillary and terminal buds of agronomic, horticultural and forestry crops.

It is another object of the present invention to provide a composition as above which imparts low necrosis and phytotoxicity levels to the crops.

It is still another object to provide a method for controlling axillary and terminal buds of agronomic, horticultural and forestry crops.

It is yet another object to provide a method for as above which imparts low necrosis and phytotoxicity levels to the crops.

In general, according to the present invention, a composition for controlling axillary and terminal buds of agronomic, horticultural and forestry crops comprises from about 5 to about 95 percent by weight of at least one first fatty alcohol having up to about 10 carbon atoms; and, from about 95 to about 5 percent by weight of at least one second fatty alcohol having at least 11 carbon atoms.

There is also provided according to the present invention, a method of controlling axillary and terminal buds of agronomic, horticultural and forestry crops, which comprises the step of contacting the crop buds with a mixture which comprises from about 5 to about 95 percent by weight of at least one first fatty alcohol having up to about 10 carbon atoms; and, from about 95 to about 5 percent by weight of at least one second fatty alcohol having at least 11 carbon atoms.

At least one or more of the foregoing objects, together with the advantages thereof over the known art relating to debudding and bud growth controlling agents, which shall become apparent from the specification which follows, are accomplished by the invention as hereinafter described and claimed.

PREFERRED EMBODIMENT FOR CARRYING OUT THE INVENTION

According to the present invention, there is provided a composition mixture which is useful in controlling axillary and terminal buds of agronomic, horticultural and forestry crops. By "controlling" it is understood to mean destroying the buds, inhibiting their growth or both. The composition according to the invention provides the unexpected result of exhibiting high activity in controlling the buds, low necrosis and phytotoxicity levels are imparted to the crop, and there is also a decreased human and animal toxicity hazard and a decreased hazard of flammability when compared to compositions heretofore known in the art.

The compositions according to the present invention include a mixture of at least one first fatty alcohol having up to about 10 carbon atoms, and preferably from about 6 to about 10 carbon atoms. Two preferred first fatty alcohol having 10 or less carbon atoms are 1-octanol and 1-decanol.

The composition mixtures also include at least one second fatty alcohol having 11 or more carbon atoms, and preferably from 11 to 14 carbon atoms. One preferred fatty alcohol useful as the second alcohol is 1-dodecanol, which has 12 carbon atoms.

It is preferred that the mixtures according to the invention include from about 5 to about 95 percent by weight of at least one of the first fatty alcohols having up to about 10 carbon atoms. It is even more preferred that the mixtures include from about 95 to about 5 percent by weight of at least one of the second fatty alcohol having at least 11 carbon atoms. It is further preferred that the mixture contain from about 10 to about 70 percent by weight of the second fatty alcohol having at least 11 carbon atoms.

There is also provided according to the present invention, a method of controlling axillary and terminal buds of agronomic, horticultural and forestry crops. The method includes contacting the crop buds with a mixture having the ingredients and ranges of ingredients as described hereinabove.

As will be appreciated by one skilled in the art, the present composition mixtures may include other ingredients such as growth regulators, emulsifiers, extenders, diluents and the like, all of which would be within the scope of the invention. Maleic hydrazide (MH) has been widely used as a growth regulator to control tobacco suckers. The MH's use has been, however, limited by its residue on tobacco leaves.

As will be more fully discussed hereinbelow, the composition mixtures according to the present invention give higher control of axillary and terminal buds with acceptable phytotoxicity and necrosis levels than those bud controlling agents heretofore used in the past. Furthermore, the health hazards due to toxicity and flammability are also lower than with those agents heretofore known. Furthermore, the composition mixtures according to the present invention unexpectedly exhibit these improved characteristics despite the fact that each individual component would by itself not exhibit all of the characteristics. Furthermore, it will be demonstrated that the compositions according to the invention unexpectedly satisfy the objects of the present invention in a manner beyond what would normally be expected based upon the performance of the mixture components individually.

In order to demonstrate the improved effectiveness of the compositions according to the present invention when compared to those compositions heretofore known in the art, a number of compositions were prepared and a number of experiments were preformed. These examples are set forth for the purpose of illustrating the present invention and are not to be construed to limit the invention to the precise compositions of the mixtures specified nor to the uses shown.

GENERAL EXPERIMENTAL

In the following examples, a number of control compositions and a number of compositions according to the invention were prepared. In order to determine phytotoxicity, it is necessary to provide a relative base of reference based upon a given agent's effect upon a group of plants. Phytotoxicity rating for purposes of this disclosure are as follows:

| Rating | Phytotoxicity Level |
| --- | --- |
| 0: | No phytotoxicity |
| 1: | 2 plants or less out of 5 plants in a plot show 2 or less small necrotic spots that are less than 5 mm in diameter; |
| 2: | 3 plants or more out of 5 plants in a plot show 2 or less small necrotic spots; |
| 3: | 2 plants or less out of 5 plants in a plot show 2 or more small necrotic spots plus 2 or less large necrotic spots that are larger than 5 mm in diameter; |
| 4: | 2 plants or less out of 5 plants in a plot show more than 2 large necrotic spots; |
| 5: | 3 plants or more out of 5 plants in a plot show more than 2 large necrotic spots; |
| 6: | Less then 10 percent of the sprayed leaf area is dead; |
| 7: | 10 to 30 percent of the sprayed leaf area is dead; |
| 8: | 30 to 50 percent of the sprayed leaf area is dead; |
| 9: | 50 to 70 percent of the sprayed leaf area is dead; |
| 10: | 70 percent or more of the sprayed leaf area is dead. |

Furthermore, percent of "sucker" control (% control) is calculated as follows:

% control = (1-fresh sucker weight of treated plot/fresh sucker weight of TNS plot) × 100, where TNS is "topped not suckered"

EXAMPLE 1

To prepare control compositions, single fatty alcohols, 1-hexanol, 1-octanol, 1-decanol, and 1-dodecanol were formulated to an emulsifiable concentrate (EC) form by individually mixing 85 percent by weight of each fatty alcohol with 15 percent by weight of polyoxyethylene (20) sorbitan monooleate. Each fatty alcohol EC was diluted to 3 percent by volume with water. Field grown, flue-cured tobacco plants at the late button stage of development were topped and sprayed with 10 ml of each diluted test emulsion with a hand-held sprayer. The spray nozzle was set to give a coarse spray. The test was designed as a randomized block design and, test plots were replicated 4 times. Each plot contained 5 plants. Tests of certain fatty alcohols or their mixtures were repeated 2 to 3 times. Data were taken as an average of 4 replications and averaged again where experiments were repeated. Evaluation of phytotoxicity was made 7 days after the spray and the final sucker (axillary bud of tobacco) counts and weight measurements were made 31 days after the treatment.

TABLE I

| SUCKER CONTROL BY LINEAR PRIMARY ALCOHOLS | | | | |
| --- | --- | --- | --- | --- |
| Fatty Alcohol (Carbon Atoms) | Observed Phytotoxicity Rating | Sucker Number Per Plant | Fresh Weight[a] | % control |
| 1-hexanol ($C_6$) | 0 | 5.6 | 385 | 4 |
| 1-octanol ($C_8$) | 0 | 2.4 | 175 | 56 |
| 1-decanol ($C_{10}$) | 1 | 1.9 | 148 | 63 |
| 1-dodecanol ($C_{12}$) | 9.5 | 1.9 | 159 | 60 |

TABLE I-continued

| Fatty Alcohol (Carbon Atoms) | Observed Phytotoxicity Rating | Sucker Number Per Plant | Fresh Weight[a] | % control |
|---|---|---|---|---|
| TNS | 0 | 5.1 | 402 | 0 |

[a]sucker fresh weight per plant in grams

The test results above (TABLE I) confirm the previous study that 1-decanol was the most active fatty alcohol which controlled tobacco suckers and 1-dodecanol caused severe phytotoxicity of tobacco leaves.

EXAMPLE 2

To demonstrate that phytotoxicity of certain mixtures of fatty alcohols containing $C_{11}$ or higher carbon number alcohols is lowered synergistically by $C_{10}$ or lower carbon number fatty alcohols, Formulation Mixtures, 1–16 inclusive, with various compositions involving 1-hexanol, 1-octanol, 1-decanol and 1-dodecanol were prepared in the same way as shown in Example 1, except Formulation Mixture 16 where the emulsifiable concentration of the fatty alcohol mixture was 80 percent by weight. All the experimental conditions and evaluation methods were same as in the Example 1. Phytotoxicity ratings of the various Formulation Mixtures are reported in TABLE II. The mixtures with 1-dodecanol content of 70 percent or higher show moderate to severe phytotoxicity. Any mixtures with 1-dodecanol content of 61 percent or lower show slight phytotoxicity that can be tolerated by growers and buyers of leaf tobacco.

TABLE II

EXAMPLE 2 FORMULATION MIXTURES AND PHYTOTOXICITY RATINGS

| Formulation Mixture | Composition (percent by weight) | | | | Phytotoxicity Rating |
|---|---|---|---|---|---|
| | $C_6$[b] | $C_8$[c] | $C_{10}$[d] | $C_{12}$[e] | |
| 1 | — | 73 | 27 | — | 0 |
| 2 | — | 46 | 54 | — | 0.5 |
| 3 | 0.5 | 42 | 56 | 1.5 | 0.5 |
| 4 | — | 23 | 77 | — | 0.8 |
| 5 | — | 39 | 57 | 4 | 0 |
| 6 | — | 28 | 63 | 9 | 0.5 |
| 7 | — | 15 | 69 | 16 | 0.5 |
| 8 | — | 2 | 75 | 23 | 1.0 |
| 9 | — | 1 | 87 | 12 | 0.5 |
| 10 | — | 23 | 27 | 50 | 1.5 |
| 11 | — | 1 | 38 | 61 | 2.0 |
| 12 | — | 1 | 29 | 70 | 3.5 |
| 13 | — | — | 15 | 85 | 6.5 |
| 14 | — | 50 | — | 50 | 1.5 |
| 15 | 2 | 22 | 64 | 12 | 0.5 |
| 16[f] | — | 2 | 75 | 23 | 0.8 |

[b]1-hexanol
[c]1-octanol
[d]1-decanol
[e]1-dodecanol
[f]80 percent EC

EXAMPLE 3

To demonstrate synergistically enhanced sucker control activity due to $C_{11}$ or higher carbon number fatty alcohol, selected fatty alcohol Formulation Mixtures were tested under the same experimental conditions as in the Example 1. The Formulation Mixtures include selected ones according to the prior art (namely, Formulation Mixtures 1, 2 and 4 and the TNS method) and selected ones according to the present invention (Formulation Mixtures 6, 8, 10 and 11). Results of the tested formulations are given in TABLE III.

TABLE III

EFFECT OF FATTY ALCOHOL MIXTURES ON SUCKER CONTROL

| Formulation Number | Number of Suckers | Sucker Fresh Weight (grams)[g] | % Control |
|---|---|---|---|
| TNS | 5.1 | 402 | 0 |
| 1 | 2.5 | 178 | 56 |
| 2 | 2.1 | 154 | 62 |
| 4 | 1.6 | 140 | 65 |
| 6 | 2.1 | 151 | 62 |
| 8 | 1.5 | 125 | 69 |
| 10 | 1.0 | 84 | 79 |
| 11 | 1.0 | 82 | 80 |

[g]per plant

Thus it can be observed that sucker control of the invention mixtures was above that expected based upon the individual fatty alcohol's abilities as discussed in Example 1 and comparable to or above that of the mixtures containing only $C_{10}$ or lower fatty alcohols. It will also be appreciated that because the invention mixtures contain less $C_{10}$ or lower alcohols than those mixtures heretofore known in the art (as shown in TABLE II) the hazards of flammability and human and animal toxicity are decreased. At the same time, the invention mixtures show comparable phytotoxicity ratings to the mixtures heretofore known in the art, or ratings that are lower than expected based upon the individual rating of the mixture's individual components and within acceptable industry standards.

EXAMPLE 4

To further demonstrate the unexpected improvement of the invention mixtures as compared with those heretofore known in the art, Formulation Mixture 16 according to the invention was further compared to Formulation Mixture 3 which is a bud control mixture widely used in the United States. The Formulations were tested at various concentrations. All other experimental conditions in this Example were the same as in Example 1 except that the final sucker evaluation was made 46 days after treatment at the end of leaf harvest. Formulation Mixture 16 at 4 percent concentration exhibited 93 percent control with only minor phytotoxicity, compared to 88 percent control with moderate phytotoxicity by Formulation Mixture 3 at 8 percent concentration, as reported in TABLE IV.

TABLE IV

CONCENTRATION EFFECTS ON SUCKER CONTROL

| Formulation Number | Spray Concentration[h] | Phytotoxicity Rating | Sucker Fresh Weight (grams)[i] | % Control |
|---|---|---|---|---|
| TNS | 0 | 0 | 606 | 0 |
| 3 | 4 | 0.3 | 319 | 47 |
| | 6 | 2.5 | 151 | 75 |
| | 8 | 4.0 | 72 | 88 |
| 16 | 3 | 0.3 | 182 | 70 |
| | 4 | 1.0 | 40 | 93 |
| | 6 | 3.5 | 21 | 96 |

[h]percent by volume
[i]per plant

EXAMPLE 5

An experiment was conducted to show that the MH rates or other growth regulator rates can be lowered by spraying tobacco plants sequentially with a fatty alcohol product followed by a MH product. All the experimental conditions were the same as in the Example 1 except that the final sucker evaluation was made 46 days after the topping and 10 cc of MH-containing solution per plant was sprayed as a fine spray onto the plant 7 days after the topping. All the large suckers over 2 cm were removed by hand before MH spray. The sequential treatment at MH rate of 54 mg a.i. (active ingredient) per plant showed a comparable activity to that of the MH treatment alone at 81 mg a.i. per plant as reported in TABLE V. Thus MH use rate can be reduced by 33 percent which in turn will reduce MH residue on tobacco leaves.

TABLE V

| Formulation Mixture | Amount Rate | Phytotoxicity Rating | % Control |
|---|---|---|---|
| 17[j] | 36 mg | 0 | 50 |
|  | 54 mg | 0 | 66 |
|  | 81 mg | 0 | 98 |
| 16/17[k] | 3/36 | 0.3 | 80 |
|  | 3/54 | 0.3 | 97 |
| TNS |  0 | 0 | 0 |

[j]potassium salt of maleic hydrazide (MH)
[k]percent Formulation Mixture 16/milligrams of potassium salt of maleic hydrazide (MH added)

Thus it should be evident that the compositions and methods of the present invention are highly effective in controlling axillary and terminal buds of the contemplated crops. The invention is particularly suited for tobacco crops, but is not necessarily limited thereto.

Based upon the foregoing disclosure, it should now be apparent that the use of the compositions and methods described herein will carry out the objects set forth hereinabove. It is, therefore, to be understood that any variations evident fall within the scope of the claimed invention and thus, the selection of specific component elements can be determined without departing from the spirit of the invention herein disclosed and described. Thus, the scope of the invention shall include all modifications and variations that may fall within the scope of the attached claims.

What is claimed is:

1. A composition for controlling axillary and terminal buds of tobacco crops comprising:

from about 15 to about 85 percent by weight of a first fatty alcohol having up to about 10 carbon atoms; and, from about 85 to about 15 percent by weight of a second fatty alcohol having at least 11 carbon atoms;

wherein no more than 40% of the crop plants to which the composition is applied exhibit necrotic spots.

2. A composition as in claim 1, comprising from about 70 to about 10 percent by weight of said second fatty alcohol.

3. A composition as in claim 1, wherein said first fatty alcohol has from about 6 to about 10 carbon atoms.

4. A composition as in claim 1, wherein said second fatty alcohol has from 11 to about 14 carbon atoms.

5. A composition as in claim 4, wherein said second fatty alcohol is 1-dodecanol.

6. A composition as in claim 1, wherein said first alcohol is selected from the group consisting of 1-hexanol, 1-octanol and 1-decanol.

7. A method for controlling axillary and terminal buds of tobacco crops, comprising the step of:

contacting the crop buds with a mixture having low phytotoxicity toward the crops comprising:

from about 15 to about 85 percent by weight of a first fatty alcohol having up to about 10 carbon atoms; and, from about 85 to about 15 percent by weight of a second fatty alcohol having at least 11 carbon atoms.

8. A method as in claim 7, comprising the further step of emulsifying said mixture prior to said step of contacting the crop buds.

9. A method as in claim 7, further comprising the steps of sequentially and alternately contacting the crop buds with said mixture and a growth regulator.

10. A method as in claim 9, wherein said growth regulator is a maleic hydrazide.

11. A method as in claim 7, further comprising the step of adding an active amount of a growth regulator to said mixture prior to said step of contacting the bud crops.

12. A method as in claim 11, wherein said growth regulator is a maleic hydrazide.

* * * * *